United States Patent [19]
Nies

[11] Patent Number: 5,725,813
[45] Date of Patent: Mar. 10, 1998

[54] PROCESS FOR THE PRODUCTION OF SPONGIOSA BONE CERAMIC SHAPED ARTICLES

[75] Inventor: Berthold Nies, Frankisch-Crumbach, Germany

[73] Assignee: Merck Patent Gesellschaft mit beschrankter Haftung, Darmstadt, Germany

[21] Appl. No.: 601,693

[22] Filed: Feb. 15, 1996

[30] Foreign Application Priority Data

Feb. 15, 1995 [DE] Germany ............ 195 04 955.1

[51] Int. Cl.$^6$ .................. B22D 11/01; A61F 2/28
[52] U.S. Cl. ............. 264/15; 264/628; 264/678; 623/16
[58] Field of Search .................. 264/66, 67, 15, 264/628, 678; 623/16

[56] References Cited

U.S. PATENT DOCUMENTS

| | | | |
|---|---|---|---|
| 4,654,464 | 3/1987 | Mittelmeier et al. | 623/16 |
| 4,926,890 | 5/1990 | Hoskins | 132/73 |
| 5,133,756 | 7/1992 | Bauer et al. | 623/16 |

OTHER PUBLICATIONS

Principles of Ceramic Processing, Second Edition, Wiley Interscience, James S. Reed, pp. 313–332, 1995.

*Primary Examiner*—Christopher A. Fiorilla
*Attorney, Agent, or Firm*—Millen, White, Zelano, & Branigan, P.C.

[57] ABSTRACT

The invention relates to a process for the production of spongiosa bone ceramic shaped articles with geometrically irregular shapes and rounded angles and edges, which have no mechanically unstable or inhomogeneous regions. The shaped articles are obtained by treating spongiosa bone ceramic pieces in a ball mill.

12 Claims, No Drawings

PROCESS FOR THE PRODUCTION OF SPONGIOSA BONE CERAMIC SHAPED ARTICLES

The invention relates to a process for the production of spongiosa bone ceramic shaped articles with geometrically irregular shapes and rounded angles and edges.

BACKGROUND OF THE INVENTION

It has been known for a relatively long time that mineralized bone which has been sintered to form a ceramic is ideally suited as bone replacement material. With bone ceramic there is naturally a very great degree of correspondence in chemical composition, structural composition and mechanical strength with natural bone. In addition, spongiosa bone ceramic is found to be particularly osteoconductive. The open, interconnecting, trabecular structure of spongiose bone ceramic promotes the growth of new bone matrix onto and into the ceramic, so that in the course of incorporation there is intensive colonization and therefore integration of the ceramic implant. Bone ceramics produced from bone of animal origin are therefore being increasingly employed as bone replacement materials in osteosynthesis and in the reconstitution of bone defects caused by illness or accident.

The production of bone ceramic from animal bone is generally carried out by first of all freeing selected bones or bone pieces mechanically from all adhering soft parts, then cutting these bones or bone pieces roughly to size by sawing, to give pieces of suitable shape and size, then mineralizing these pieces by the removal of all other organic components, and finally carrying out the ultimate shaping operation. The mineralization process begins first of all with the bones being boiled out several times in water. Subsequent treatment can be carried out, for instance, with fat-dissolving or protein-dissolving solvents, and/or with the aid of hydrogen peroxide, as described for example in EP 0 141 004. Methods which have proved to be particularly simple and effective are those of pyrolytic mineralization, in which the action of heat decomposes the organic component of the bone, and the resulting carbon is subsequently burnt to completion in excess oxygen. For the bone pyrolysis, temperatures of between 500° and 1000° C. are common. Following the mineralization of the bone, it is sintered to give the ceramic, with temperatures of between 800° and 1400° C. being customary. It is only through sintering that the material acquires the desired ultimate strength. In the course of the procedures mentioned, particular care must be taken to ensure that the porous structure of the original bone is retained as far as is possible. For the conversion of spongiose bone material to spongiosa bone ceramic, a preferred option is to proceed in accordance with a process set out in DE 37 27 606, in which a specific temperature regime and reductive or oxidative character of the atmosphere enables particularly gentle pyrolysis.

Subsequently, shaped articles of defined geometry and dimensions are fashioned from the rough spongiosa bone ceramic pieces by sawing or milling. Examples of common commercial forms are cubes, rectangular solids and cylinders having volumes of from about 0.25 to 4.25 $cm^3$.

The possible yield of such shaped articles, however, based on the original rough material, is extremely low. Owing to the nature-imposed shape and size of the spongiosa-containing bone parts, only a small proportion of the overall spongiose region of the rough bone is suitable and accessible for the production of the shaped articles. Cortical substance, growth cartilage, inhomogeneous and mechanically unstable regions must be removed. Frequently, such regions cannot be recognized from the outside, so that it is not until the sawing or milling stage that the shaped articles fracture, or these articles, having been recognized as unsuitable, are rejected after this operation.

The geometrically defined shaped articles mentioned all have sharp angles and edges. In the angle and edge regions, the porous spongiosa ceramic is naturally highly sensitive, with the result that, for example during clinical use, fracture and abrasion occur very readily.

In addition to unwanted changes in shape by the fracture of angles and edges, abraded particles at the implant site can give rise to unwanted reactions. This danger exists in particular in the case of the "press-fit" implantation of such shaped articles in bone defects which have been milled to the appropriate dimensions.

In addition, practical experience in clinical use of spongiosa bone ceramic shaped articles has shown that an urgent need for predetermined geometries and dimensions exists only in a few cases. Frequently the surgeon, prior to or during implantation, works on the shaped articles in order to adapt them in shape and size to the actual circumstances of the implant site. Here too, the unwanted incorporation of fine particles is often unavoidable. Moreover, in cases where bone defects of relatively large volume are filled, it would be much more advantageous to have available a relatively large number of spongiosa bone ceramic shaped articles with geometrically irregular shapes and rounded angles and edges, in order thus to fill the defect.

SUMMARY OF THE INVENTION

It has now been found that spongiosa bone ceramic shaped articles desirable for this purpose, having geometrically irregular shapes and rounded angles and edges, and without mechanically unstable regions, can be obtained by carrying out the shaping operation of spongiose bones, which have been roughly pre-shaped into pieces and then mineralized and sintered to form a ceramic, by treating the pieces in a ball mill.

The invention thus provides a process for the production of spongiosa bone ceramic shaped articles, in the course of which spongiose bones which have been roughly pre-shaped into pieces are mineralized by the removal of all organic components, the mineralized bone matrix is then sintered to form the ceramic, and then the final shaping operation is carried out, which process is characterized in that the shaping operation of the bone ceramic pieces is carried out by treatment in a ball mill, mechanically unstable regions of the bone ceramic being abraded to give geometrically irregular shaped articles with rounded angles and edges.

The process according to the invention proceeds initially in a known manner, in particular in accordance with the process of DE 37 27 606, in order to mineralize the bone material and sinter it to form the ceramic. For this purpose the selected bone material, preferably heads of bone from newly slaughtered cattle which have been prepared in cuboid pieces by removal of soft parts and sawing roughly to size, is initially boiled out in water several times. The bone pieces are then dried for a number of hours, pyrolyzed under nitrogen, burnt to completion in air or oxygen and then subjected to final sintering. Before final sintering it is possible, as described in DE 40 28 683, to provide for a treatment step with an aqueous solution of an organic acid, especially citric acid, by means of which calcium oxide components are leached out of the material.

In accordance with the invention, the final treatment of the bone ceramic pieces to remove mechanically unstable regions and for the actual shaping operation to give shaped articles with rounded angles and edges is carried out in a ball mill. For this purpose the bone ceramic pieces are used just as they are obtained from the sintering process. Prior size reduction by means of saws, mills or jaw crushers is advantageous, being directed on the one hand at the removal of any remaining regions of cortical substance and growth cartilage and at the desired order of size of the shaped articles. Equally suitable as well are fragments and offcuts obtained from the production of shaped articles of defined geometry.

The roughly pre-shaped spongiosa bone ceramic pieces are then introduced into a common commercial ball mill in a quantity which corresponds to its capacity, where they are subjected to the more or less intense treatment of the final shaping operation. A typical ball mill is composed essentially of a cylindrical vessel which is made of a sufficiently hard material and can be tightly closed with a lid. This vessel is rotated about its axis on a roller mechanism at a speed of rotation which, advantageously, can be regulated. Alternative designs are centrifugal, vibratory and planetary ball mills. Such ball mills typically have a volume of between 1 and 15 l.

It is common for grinding media of a sufficiently hard material, generally in the shape of balls, to be added to the mill charge during treatment. The grinding balls typically have diameters of between 9 and 50 mm. It is advantageous for the ball mill and grinding balls to consist of hard porcelain or $Al_2O_3$. The latter material is considerably harder than bone ceramic, so that no wear of the mill or balls or resulting contamination of the mill charge need be expected.

The intensity and duration of processing in the ball mill, and the possible addition and size of the grinding balls, are dependent on the primary size and quality of the bone ceramic pieces, on the degree of removal of material desired, and on the required final size. Slow running of the mill for a long period with only small grinding balls or none at all is more gentle, and is preferred in the case, for instance, of treating spongiosa ceramic of low density and strength. Brief intense treatment with relatively large balls can be expedient in the case of hard material of greater density. Examples of typical milling conditions are a running time of from about 2 to 6 hours with grinding media or a running time of from about 6 to 18 hours without grinding media in a ball mill with a capacity of 10 l which is filled with a bulk volume of about 5 l of mill charge.

In addition to "dry" treatment in the ball mill, it can be advantageous to carry out a "wet" shaping operation. In this case an auxiliary milling liquid is additionally added to the mill charge, it being possible for the volume ratio of mill charge to liquid to be in the range from 0.5 to 2.5. By this means it is possible for the treatment to be even more gentle. Moreover, to a great extent the abraded particles are detached and/or held in suspension away from the treated bone ceramic pieces by such "wet" shaping. A liquid preferably employed is water. It is also possible to use organic solvents as auxiliary milling liquid. Preferably alcohols such as, in particular, methanol and ethanol are suitable. It can also be advantageous to employ an aqueous salt solution, preferably of calcium salts or phosphate salts, as auxiliary milling liquid. By this means it is possible, if desired, chemically to modify the bone ceramic shaped articles as early as during the milling operation, for instance by additional coating of the surface with calcium ions, whereby the incorporation of such an implant article can be influenced positively.

The result of the treatment according to the invention in the ball mill is the complete removal of those parts of the roughly pre-shaped bone ceramic articles which are able to tolerate little or no mechanical stress. The articles, depending on the nature and duration of the treatment, are rounded off to a greater or lesser extent. In particular, the weak points at the exposed angles and edges are removed and can no longer break away and/or release particles in the course of subsequent clinical use. Following treatment in the ball mill, from about 60 to 80% of the bone ceramic material used remains as rounded, irregularly shaped articles. These irregular articles have a greater homogeneity, in terms of porosity, than the material originally employed. Because of the machining, only the spongiose regions of relatively high density and mechanical stability remain as shaped articles, since all highly porous and mechanically unstable regions have been abraded.

It will be understood of course that it is possible to employ not only ball mills but also other milling apparatus and/or treatment techniques, provided they lead to a similar result.

The treatment according to the invention is concluded by sieving out and then thoroughly washing out the abraded material. After adequate washing, the articles treated in accordance with the invention produce no notable abraded material either during storage or in the course of clinical handling. The reliable removal of all of those spongiosa regions with an above-average high porosity and a low capacity for withstanding stress leaves a material which is of markedly higher compressive strength, a quality which is essential for clinical use. The considerably improved utilization of the bone material employed is a further important advantage of the process according to the invention, which increases the economic viability of the use of spongiosa bone ceramic in endoprosthetics.

In the foregoing and in the following examples, all temperatures are set forth uncorrected in degrees Celsius; and, unless otherwise indicated, all parts and percentages are be weight.

The entire disclosure of all applications, patents and publications, cited above and below, and of corresponding German application No. DE 195 04 955.1, filed Feb. 15, 1995 is hereby incorporated by reference.

EXAMPLES

Example 1

Raw heads of bone, freed from soft parts, from newly slaughtered cattle are sawed into cuboid pieces with dimensions of roughly 30×30×100 mm which are boiled out with water three times for about 1 hour.

The bone pieces are then dried at 110° C. for 6 hours. They are subsequently heated under a nitrogen atmosphere to 450° C. over the course of 9 hours. During a subsequent 20-hour heating period from 450° C. to 600° C., the atmosphere is changed over in linear progression to atmospheric oxygen, after which heating is continued to 900° C. over the course of 5 hours. After cooling, the pieces are placed in a bath of 5% by weight citric acid solution (10 l per kg of bone material) and treated in the agitated bath at a temperature of 20° C. for a period of 3 hours. After this treatment, the pieces are rinsed 3 times with demineralized water. For final sintering, the pieces are heated to 1250° C. over the course of 21 hours, held at this temperature for 3 hours, and then left to cool down.

The resulting bone ceramic pieces exhibit the unchanged porous structure of the original spongiose bone. According to X-ray analysis the ceramic has a hydroxyapatite content of about 99%. The resulting bone ceramic pieces are milled using a hollow milling cutter with an internal diameter of 10 mm to give cylinders which are then brought to a length of 10 mm. In the course of this procedure there is no need to watch out for homogeneity, growth cartilage, cracks, etc., as is necessary in the production of geometrically defined shaped articles.

The quantity of such cylinders which corresponds to a bulk volume of approximately 5 l is introduced into a customary commercial ball mill made of $Al_2O_3$ with a capacity of 10 l and is milled for 18 hours at 30 revolutions per minute without the addition of grinding media.

The shaped articles are then washed three times with demineralized water in an ultrasound bath, during which they are shaken several times. The shaped articles are autoclaved at 122° C. for 15 minutes in a flow of steam. The material is subsequently dried and freed from organic contaminants at 300° C. for 18 hours with ingress of air. Well-rounded to approximately spherical shaped articles are obtained which are of high homogeneity and mechanical strength and are sealed five at a time into vacuum-formed packs.

Example 2

The procedure is as in Example 1 but in this case waste material, fragments and rejects from the production of geometrically defined shaped articles are used. Articles of different shape and size with well-rounded angles and edges are obtained, which are of high homogeneity and mechanical strength.

Example 3

The procedure is as in Example 1 but in this case the sintered material, after removal of regions of cortical substance, is reduced in size in a jaw crusher to pieces of from 1 to 2 cm in size, which are then treated in the ball mill for 3 hours with the addition of 5 $Al_2O_3$ balls of 3 cm diameter. in this case, pieces of high density and variable shape are obtained which are passed through a sieve for screening. After removal of the abraded material in an ultrasound bath followed by autoclaving and drying, the pieces are packaged as units of 20 g each.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the production of spongiosa bone ceramic shaped articles, which comprises mineralizing spongiosa bones in rough preshape pieces by the removal of all organic components, sintering the mineralized bone pieces to ceramic form, and then shaping the bone pieces in ceramic form by treatment in a ball mill made of $Al_2O_3$ with the addition of balls made of $Al_2O_3$, in the presence of water, an aqueous salt solution or an organic solvent, whereby mechanically unstable regions of the bone pieces in ceramic form are abraded to give geometrically irregular shaped articles with rounded angles and edges.

2. The process of claim 1, wherein the spongiosa bones are heads of bone from newly slaughtered cattle.

3. The process of claim 1, further comprising, before final sintering, treating the bone pieces with an aqueous solution of an organic acid to leach out calcium oxide components.

4. The process of claim 3, wherein the organic acid is citric acid.

5. The process of claim 1, wherein the balls made of $Al_2O_3$ have a diameter of between 9 and 50 mm.

6. The process of claim 1, wherein the shaping in the ball mill is conducted for from about 2 to 6 hours in a ball mill with a capacity of 10 liters and a bulk volume of about 5 liters of mill charge.

7. The process of claim 1, wherein the volume ratio of solids to liquids in the mill charge is 0.5 to 2.5.

8. The process of claim 1, wherein the shaping in the ball mill is conducted in the presence of water.

9. The process of claim 1, wherein the shaping in the ball mill is conducted in the presence of an alcohol.

10. The process of claim 1, wherein the shaping in the ball mill is conducted in the presence of a calcium or phosphate salt solution.

11. A process for the production of spongiosa bone ceramic shaped articles, which comprises shaping bone pieces, mineralized and sintered to ceramic form, by treatment in a ball mill containing balls made of $Al_2O_3$, in the presence of water, an aqueous salt solution or an organic solvent.

12. The process of claim 11, wherein mechanically unstable regions of the bone pieces in ceramic form are abraded to give geometrically irregular shapes articles with rounded angles and edges.

* * * * *